(12) United States Patent
Halpern et al.

(10) Patent No.: US 6,997,861 B2
(45) Date of Patent: Feb. 14, 2006

(54) METHODS FOR TREATING SOLID TUMORS USING NEUTRON THERAPY

(75) Inventors: David Halpern, Alpharetta, GA (US); Steven K. Jacobs, New Canaan, CT (US)

(73) Assignee: Isotron, Inc.

( * ) Notice: Subject to any disclaimer, the term of this patent is extended or adjusted under 35 U.S.C. 154(b) by 0 days.

(21) Appl. No.: 10/766,744

(22) Filed: Jan. 27, 2004

(65) Prior Publication Data

US 2004/0184988 A1 Sep. 23, 2004

Related U.S. Application Data

(63) Continuation of application No. 10/036,767, filed on Nov. 8, 2001, now Pat. No. 6,685,619, which is a continuation of application No. 09/394,234, filed on Sep. 13, 1999, now Pat. No. 6,319,189.

(51) Int. Cl.
*A61N 5/00* (2006.01)

(52) U.S. Cl. ........................................... 600/3
(58) Field of Classification Search ............... 600/1–8
See application file for complete search history.

(56) References Cited

U.S. PATENT DOCUMENTS

| | | | |
|---|---|---|---|
| 6,319,189 B1 * | 11/2001 | Halpern et al. | 600/3 |
| 6,551,232 B1 * | 4/2003 | Rivard | 600/3 |
| 6,685,619 B2 * | 2/2004 | Halpern et al. | 600/3 |

OTHER PUBLICATIONS

Yosh Maruyama et al., "Work in Progress: 252CF Neutron Brachytherapy for Hemispheric Malignant Giloma", Radiology, vol. 145, No. 1, pp. 171-174, 1982.*
J.G. Wierzbicki et al., "Measurement of Augmentation of 252CF implant by 10B and 157 Gd Neutron Capture", Med. Phys., 21 (6), pp. 787-790, Jun. 1994.*
Barthelemy et al., "The Development of Californium-252 Sealed Sources at the Commissariat A L'Energie Atomique", Nuclear Technology, vol. 26, No. 2, pp. 201-214, 1975.*

* cited by examiner

Primary Examiner—John P. Lacyk
(74) Attorney, Agent, or Firm—DLA Piper Rudnick Gray Cary US LLP

(57) ABSTRACT

The invention described herein comprises a method of treating a subject having a disorder characterized by the presence of one or more tumors comprising inserting a miniaturized concentrated neutron emitting source into said tumor(s) for a time sufficient to irradiate the cells of the tumor(s). The invention method can be employed in the treatment of both malignant and non-malignant tumors and is especially useful in the treatment of malignant tumors found in the brain, prostate, and other internal organs. A preferred neutron source is californium-252. The majority of the tumor can be surgically removed prior to insertion of the neutron emitting source. In a further embodiment of the invention, a neutron capture compound can be localized to the cells of the tumor prior to insertion of the miniaturized neutron emitting source in order to augment the effects of neutron therapy.

18 Claims, 2 Drawing Sheets

METHODS FOR TREATING SOLID TUMORS USING NEUTRON THERAPY

CROSS-REFERENCE TO RELATED APPLICATION

This application is a Continuation application, under 35 U.S.C. § 120, of U.S. application Ser. No. 10/036,767, filed on Nov. 8, 2001, which is now U.S. Pat. No. 6,685,619, which was a continuation application of U.S. application Ser. No. 09/394,234 filed on Sep. 13, 1999, which is now U.S. Pat. No. 6,319,189, which are incorporated herein by reference in their entirety.

FIELD OF THE INVENTION

The present invention generally relates to methods for treating disorders characterized by the formation of tumors, including cancer.

BACKGROUND OF THE INVENTION

Loss of normal control of cellular proliferation results in unregulated cell growth and, often, the formation of cellular masses commonly known as tumors. Tumors may be malignant or non-malignant. The cells composing malignant tumors often exhibit a lack of normal differentiation and possess the ability to invade local tissues and metastasize, whereas in non-malignant tumors the mass of cells is generally localized. Malignant tumors can develop in any organ at any age and, even with treatment, often result in the death of the subject While not typically posing a threat to life, non-malignant tumors can impose severe restrictions on normal physiological function.

Tumors are typically treated by surgical removal, radiation, and/or chemotherapy. Surgery is the oldest effective form of tumor therapy and can often result in a complete cure, depending of the type and nature of the tumor Many tumors, however, occur in locations and/or number that make surgery impossible or impractical. Also, surgical debulking is not guaranteed to remove all abnormal cells, particularly in the case of tumors located in the brain where maximum preservation of normal tissue is desired. Residual abnormal cells pose an increased risk of tumor re-growth and/or metastasis.

Radiation therapy is often used as an adjunct to surgery. Various types of radiation, both from external and implanted sources, have been used with some success. Low linear-energy-transfer (LET) sources, such as beta particles and gamma rays, require the presence of oxygen for their pharmacologic activity. Many tumors, however, are hypoxic due to reduced collateral blood vessel growth into the tumor interstitia, limiting the effectiveness of low LET sources and requiring repeated treatments over extended periods of time to produce any significant reduction in tumor cells.

High LET sources, such as neutrons, do not require oxygen to be effective. External beam, fast neutron therapy was widely tested in the 1970s (see, for example, Laramore, et al, Cancer 42:96-103, 1978 and Catteral and Bentley, Fast neutrons in the treatment of cancer, New York, Brune & Stratton, 1979). Unfortunately, significant radiation damage occurred to normal tissues, and patients often died from widespread radiation-induced necrosis.

Brachytherapy using an implantable neutron source has been used as an alternative to external beams. Many neutron-emitting isotopes are unsuitable for brachytherapy, however, because of short half lives and low energy. The transplutonium radioactive isotope californium-252($^{252}$Cf) is an exception, having a half-life of 2.6 years and emitting fast neutrons with an average energy of 2.3 MeV. While this technique has shown some promise in the treatment of a small number of tumor types, notably those found in the cervix or oral cavity, the relatively large size of the neutron source has limited the use of this technique.

Accordingly, there is a need in the art for new methods of treating tumors using neutrons. The present invention addresses that need.

BRIEF DESCRIPTION OF THE INVENTION

The present invention overcomes many of the problems in the art by providing a method of treating a subject having a disorder characterized by the presence of one or more tumors comprising inserting a miniaturized concentrated neutron emitting source into said tumor(s) for a time sufficient to irradiate the cells of the tumor(s). The invention method can be employed in the treatment of both malignant and non-malignant tumors and is especially useful in the treatment of malignant tumors found in the brain, cervix, oral cavity, esophagus, prostate, and other internal organs. A preferred neutron source is californium-252. In one alternative embodiment of the invention, the majority of the tumor can be surgically removed prior to insertion of the miniaturized neutron emitting source. In a further embodiment of the invention, a neutron capture compound can be localized to the cells of the tumor prior to insertion of the miniaturized neutron emitting source in order to augment the effects of neutron therapy.

DETAILED DESCRIPTION OF THE INVENTION

Figure 1:
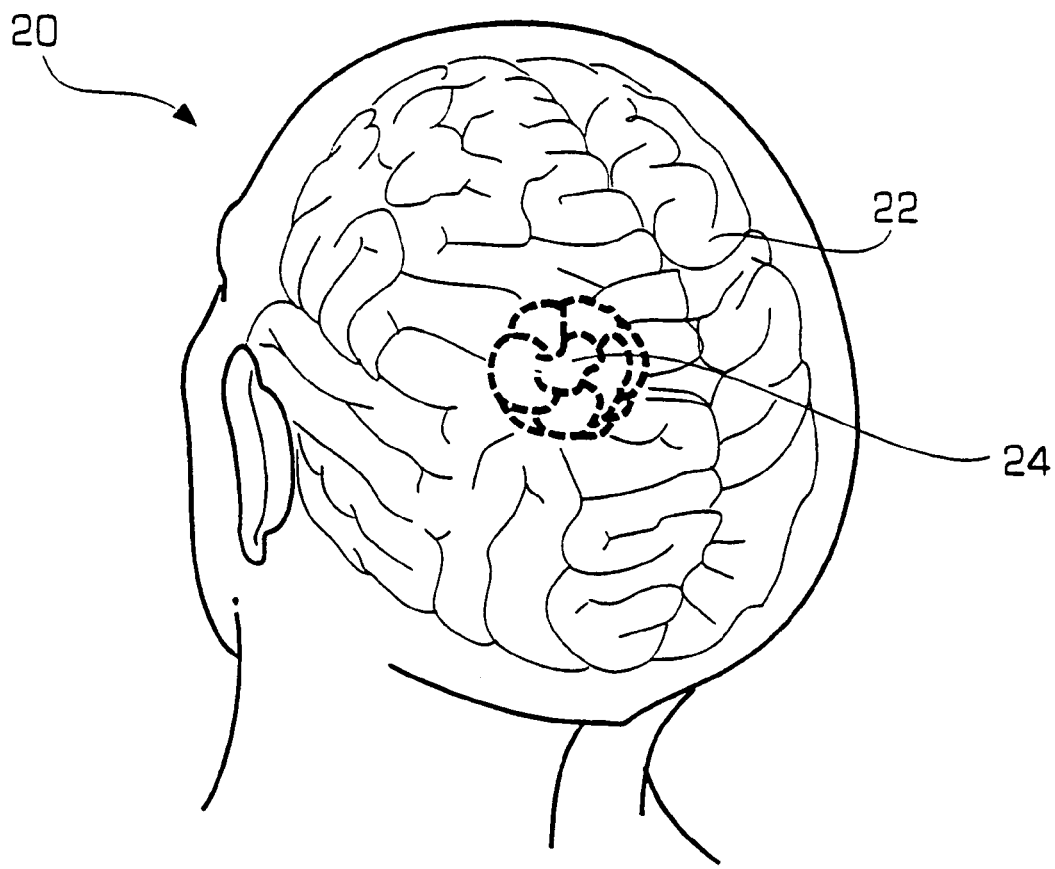
FIG. 1 is a diagram illustrating a patient with a brain tumor that may be treated using the neutron brachytherapy device in accordance with the invention.

In accordance with the present invention, there is provided a method of treating a subject having a disorder characterized by the presence of one or more tumors comprising inserting one or more miniaturized concentrated neutron emitting source(s) into the tumor(s) and maintaining the source(s) in the tumor for a time sufficient to eradicate the tumor cells. Subjects who could benefit from treatment using the method of the invention include humans and animals such as cats, dogs, and the like.

Suitable disorders for which the invention method is useful include those characterized by the presence of malignant tumors, i.e. cancer, or non-malignant tumors. The term "malignant tumor" or "cancer", as used herein, generally refers to an abnormal solid mass of tissue that is not inflammatory, arising without obvious cause from cells of preexistent tissue, possessing no physiologic function, and tending to infiltrate and/or metastasize to other parts of the body. Such tumors will usually result in the death of the subject. Malignant tumors can arise from a variety of cell types and can occur anywhere in the body. Common sites for malignant tumors include the brain, lung, bladder, pancreas, prostate, intestine (including the small intestine and colon), stomach, thyroid gland, ovary, breast, kidney, and the like. The method of the invention is particularly well suited to the treatment of cancers occurring in the brain, including glioblastomas, astrocytomas, schwannomas, malignant meningiomas, oligodendrogliomas, ependymomas and the like, all of which arise from brain cells, as well as metastatic tumors of the brain, which commonly arise from the lung, breast, prostate, skin, or GI tract.

The invention method employs a neutron emitting source, preferably californium-252($^{252}$Cf). $^{252}$Cf is particularly well suited to use in the invention method due to its relatively long half-life of 2.6 years and because it emits fast neutrons in the range of about 1 MeV to about 5 MeV, with an average of about 2.3 MeV. Neutrons emitted from the source interact with the tumor cells and form recoil protons by colliding with cellular hydrogen atoms. The recoil protons, in turn, interact with other intracellular molecules, such as proteins and nucleic acids, destroying key chemical bonds and resulting in death of the cell.

The possibility of using neutron emitting sources therapeutically has been under investigation for some time, but life-threatening side effects have limited their potential. Externally generated neutron beams have been tested (see Parker, et al, Am J Radiol. 127:331–335, 1976; Laramore, et al, Cancer 42:96–103, 1978; Catteral And Bentely, Fast neutrons in the treatment of cancer, New York, Grune & Stratton, 1979; Catteral, et al, Int J Radiat Oncol Biol Phys 6:261–266, 1980, and Batterman, Int J. Radiat Oncol Biol Phys 6:333–335, 1980, all of which are incorporated herein in their entirety) with some level of success. However, because external neutron beams cannot be focused on a tumor, they do considerable damage to normal tissue, and many test subjects died of widespread radiation-induced necrosis of the brain. Implantable neutron-emitting sources (2.8 mm×23 mm) have also been studied with some success, however the relatively large size of the source has made such treatment suitable only to the treatment of tumors in large, accessible body cavities such as the cervix and throat (see, for example, Maruyama and Beach, Int J Radiat Oncol Biol Phys 12:761–770, 1986; Maruyama, et al, Cancer 68:1189–1197, 1991; and Maruyama, et al, Cancer 71:3932–3937, 1993, all of which are incorporated by reference herein). Patchell, et al (Br J Radiol 70:1162–1168, 1997) have tested implanted $^{252}$Cf in the treatment of glioblastomas. However, the large size of the sources (2.8 mm×23 mm) and the limited amount of $^{252}$Cf contained therein (30 µg) required that the implants remain in place for an average of 29.4 hours, greatly increasing risk of infection and radiation-induced necrosis of the brain, which were observed in a significant number of test subjects. (See also Maruyama, et al, Am J Clin Oncol 5:589–591, 1982; Chin, et al, J Neurooncol 2:341–347, 1984).

In contrast, the present invention method employs a miniaturized concentrated $^{252}$Cf source that provides the medical practitioner with a method for treating tumors that is highly efficacious while having a significantly reduced risk of serious side effects. In addition, the small size of the neutron emitting source employed in the invention method allows the skilled practitioner to insert more than one source into the tumor area, thus increasing the effective localized dose of radiation and further reducing the necessary exposure time.

$^{252}$Cf may be prepared according to a number of techniques known in the art (see, for example, Martin, et al, Appl. Radiat. Isot. 48:1567–1570, 1997). In the process developed at Savannah River Laboratory (SRL), palladium (Pd) is deposited onto a fine precipitate of californium oxalate ($Cf_2(C_2O_4)$) in aqueous solution. The Pd-coated particles are dried, calcined to Pd-coated $Cf_2O_3$, pressed into a pellet at 50% of the desired density, sintered at a predetermined temperature of about 1300° C., pressed again to 90% of the desired density, and finally pressed into a capsule of platinum-iridium alloy. The source made by this process has very low concentration (<0.1 wt %) of $^{252}$Cf. Recently, a much improved process has been developed by the Radiochemical Engineering Development Center (REDC) at Oak Ridge National Laboratory (ORNL). The REDC process diverges at the sintering step. Instead of sintering at 1300° C., the pellet is heated to 1600° C., which melts the Pd—$Cf_2O_3$ mixture. After cooling, the melted pellet material is sufficiently strong and malleable to roll into a thin wire on a jeweller's rolling mill. REDC is now routinely making 1.1 mm square wire with a nominal loading of 500 µg $^{252}$Cf per inch (0.6 wt % $^{252}$Cf). The 1.1 mm wire can be further swaged into smaller wire which will then be used to fabricate the minaturized source. The neutron emitting source may be any size and shape that allows it to be inserted into the tumor to be treated. The preferred size of the neutron emitting source is a cylinder with an outside diameter of 0.5–2 mm and a length of about 3–6 mm. The preferred concentration of $^{252}$Cf is between 100 µg and 1 mg, a significant improvement over currently available sources (Martin, et al, Appl Radiat Isot 48:1567–1570, 1997). The nominal intensity of a 100 µg neutron emitting source is approximately $2.3 \times 10^8$ neutrons per second. Thus, the exposure time required to irradiate tumor cells, causing their death, may be significantly shortened from about 30 hours to about 1–10 hours. A shorter exposure time not only greatly simplifies the overall procedural requirements but also will likely reduce the risk of side effects (i.e. necrosis, infection) that have prevented the practical and wide spread use of neutron therapy. In addition, because of its small size, multiple sources can be inserted and used during a treatment procedure. In accordance with the invention, one or multiple source may be positioned in the tumor at the same time to treat the tumor. The multiple insertion of sources will result in a more desirable dose distribution in and around the tumor. The positioning of multiple sources in a tumor will further reduce the treatment time.

The invention method may be used in the event a tumor has been surgically removed and subsequently re-grows. Methods of surgically removing tumors are well known in the art. Methods of removing tumors from the brain are described in, for example, Kelly, Computer-Directed Stereotactic Resection of Brain Tumors, Neurosurgical Operative Atlas, Vol. 1, Am. Assoc Neuro Surg, 1991, and Tengachary, Frontal Lobectomy, Neurosurgical Operative Atlas, Vol. 3, Assoc Neuro Surg, 1993, (both of which are incorporated by reference herein), for example. Now, an example of the device that may be used to carry out the method of treatment in accordance with the invention will be described.

FIG. 1 is a diagram illustrating a patient's head 20. The diagram shows the patient's brain 22 with a deep seated tumor 24 that may be treated using the neutron brachytherapy device in accordance with the invention. In one typical treatment, the surgeon may surgically remove a majority of the tumor, known as tumor debulking. The neutron brachytherapy device in accordance with the invention may then be used to kill the remaining tumor cells (typically on the periphery of the tumor) instead of a conventional radiation or chemotherapy treatment. The neutron brachytherapy device reduces the damage to the surrounding healthy cells so that the amount of killing effect that can be applied to the tumor cells is increased without the undesirable side effects of the conventional radiation or chemotherapy treatments. The neutron therapy using the neutron brachytherapy device in accordance with the invention may also be combined with other treatment modalities such as boron neutron capture therapy (BNCT).

In some situations, the tumor, due to its size or location in the brain, is inoperable so that the patient is typically left to radiation or chemotherapy treatments. These treatments do not adequately treat the tumor cells since some brain tumors, such as a glioblastoma multiforme, often contain hypoxic cells that do not respond to the conventional radiation or chemotherapy treatments. The neutron brachytherapy device in accordance with the invention may be used to shrink the previously inoperable tumor sufficiently so that the tumor may then be removed or de-bulked by the surgeon during a surgical procedure. In this situation, the neutron brachytherapy device may also be used after the debulking procedure to kill the tumor cells remaining after the debulking procedure.

The neutron brachytherapy device used in the method of the invention generates fast neutrons at energy levels of about 1–5 MeV of energy. The neutrons exiting the neutron brachytherapy source strike hydrogen atoms in the tumor cells, and the resulting charged hydrogen nuclei (i.e. recoil protons) are capable of breaking chemical bonds of essential molecules (e.g. DNA) in the tumor cell and thus damage or kill the tumor cell. In this manner, the neutron brachytherapy device kills the tumor cells via the recoil protons produced by the elastic collisions between the source neutrons and the hydrogen nuclei in tissue. Now, the operation of the neutron brachytherapy device in accordance with the invention will be described.

Figure 2:
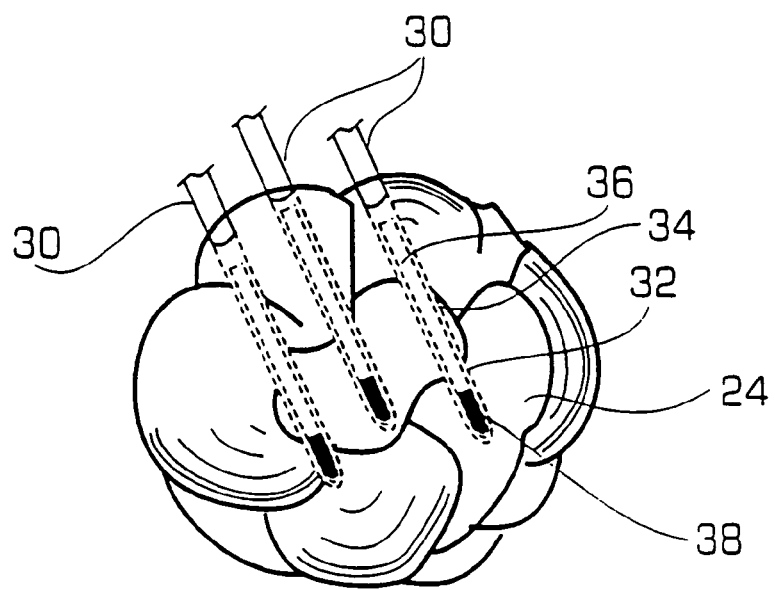
FIG. 2 is a diagram illustrating one or more neutron sources in accordance with the invention placed in a tumor to kill or damage the tumor cells.

FIG. 2 is a diagram illustrating an example of one or more neutron brachytherapy devices 30 used in accordance with the invention and placed in the tumor 24 to kill or damage the tumor cells. For purposes of illustration only, the tumor 24 is shown without the surrounding healthy brain cells. In this example, there are three neutron brachytherapy devices inserted into the tumor cells based on the size and shape of the tumor as well as the dose distribution of each of the neutron sources. The number of neutron sources inserted into the tumor may be varied. As shown, each neutron brachytherapy device 30 may include a hollow catheter 32 with a closed end that has been inserted into a predetermined portion of the tumor by the surgeon. A source wire 34 may fit within the catheter and is inserted into the catheter by a computer-controlled remote afterloader system. The source wire 34 may include a guide wire 36 and a neutron source capsule 38 that may be attached to the end of the guide wire. The neutron source capsule may contain the neutron generating material, that may be $Cf^{252}$ in a preferred embodiment. The neutron generation material may radioactively decay to generate helium gas and the neutrons that indirectly damage the tumor cells. The neutron sources may be left in the tumor for about 1–5 hours to complete the treatment. Once the treatment has been completed, the brachytherapy devices 30 and the catheters may be removed from the tumor and the entry points for the catheters in the patient are sewn up. Now, the source wire and guide wire will be described in more detail.

Figure 3:
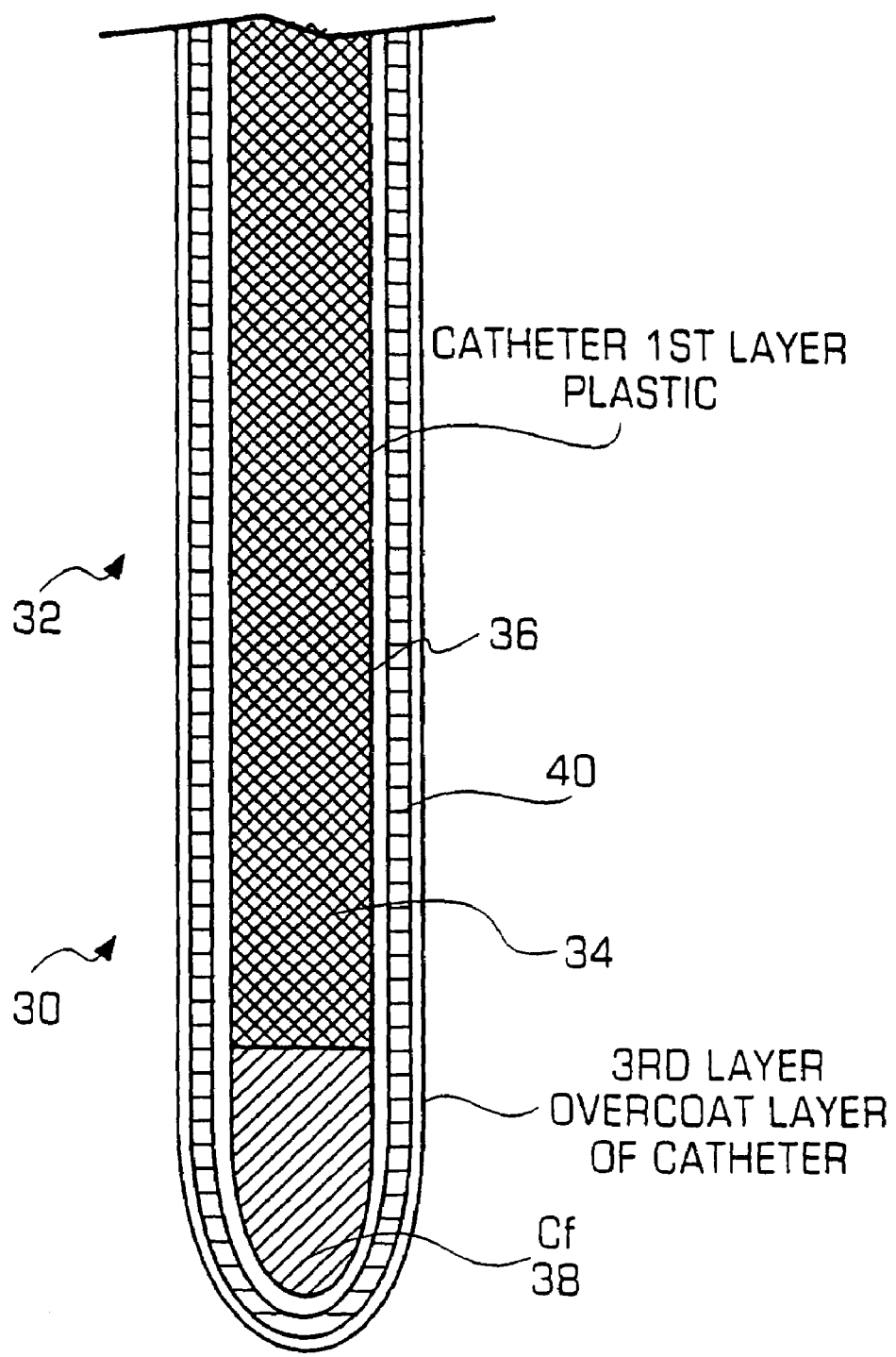
FIG. 3 is a diagram illustrating an example of a neutron source in accordance with the invention.

FIG. 3 is a diagram illustrating an example of the brachytherapy device 30 in accordance with the invention. In this example, the catheter 32 and the source wire 34 that fits into the catheter are shown. To prevent an accident, such as the source piercing the end of the catheter and being exposed to the patient, the end of the radiation material 38 may be rounded. The catheter 32 with the closed end ensures that the source wire never comes into contact with the fluids of the patient so that the source wire may be used for multiple patients without trying to clean the source wire. A neutron source wire is very difficult to clean since it must be done in a hot cell to prevent neutron exposure. To maintain the flexibility of the source wire and catheter (so that the catheter may be positioned in difficult locations) while increasing the safety of the neutron brachytherapy device, the device 30 may include a coiled metallic wire 40 wrapped around the catheter material. The coiled wire increases the strength of the source wire, permits the source wire and catheter to be bent to get to difficult locations and prevents the source wire and catheter from becoming kinked. A kinked catheter or source wire might cause the neutron source 38 to be stuck within the patient so that the patient receives an unwanted dose of neutrons.

Returning to a description of the method, the neutron emitting source is inserted into the tumor or into the resected tumor space by means of one or more stereotactically guided catheters. Suitable catheters can be obtained from sources known in the art. A preferred catheter and insertion system is described in U.S. Pat. No. 6,352,500 entitled Neutron Brachytherapy Device and Method that was filed on Sep. 13, 1999 (incorporated by reference herein in its entirety). Stereotactic guidance systems are also well known in the art. A preferred system is Stealthsystem (Sofamor Danek, Memphis, Tenn.).

Methods for inserting the neutron emitting source into a tumor are described in the Examples below. Briefly, the tumor is located using, for example, magnetic resonance imaging (MRI) and/or CT scans. For a tumor in the brain, the scalp over the tumor is reflected and burr holes are drilled in the skull. A stereotactic guidance system is used to localize one or more catheters in the tumor space and then a neutron emitting source is automatically loaded into the pre-placed catheters using a remote afterloader. Because of the high intensity of neutrons contained within the source, the remote afterloader is preferably located in a separate room. The neutron emitting source(s) is left in the tumor or tumor margin for a period of time (generally 30 minutes to 10 hours), then the source is retracted and the catheters removed.

In an alternative embodiment, the invention method can be used in conjunction with neutron capture therapy (NCT). NCT as a concept for treating cancer has been known for many years (see, Locher, Am J Roent 36:1–13, 1936). A stable isotope of boron-10 ($^{10}B$) or gadolinium-157 ($^{157}Gd$) is preferentially localized to tumor cells using targeted compounds. The tumor is then exposed to a thermal neutron field, resulting in neutron capture reactions and the production of localized high-LEI radiation from alpha and $^7Li$ particles, in the case of $^{10}B$, or gamma rays and low energy electrons, in the case of $^{157}Gd$. The products of the neutron capture reaction are very harmful to cells, but of short range (comparable or less than the dimension of the average cell). The majority of the ionizing energy released is, therefore, confined to the vicinity of the boron- or gadolinium-containing compound, lessening the damage to surrounding healthy tissue. Because some of the fast neutrons emitted from the $^{252}Cf$ source will be thermalized in the vicinity of the tumor, the use of neutron capture agents ($^{10}B$ or $^{157}Gd$) during a neutron brachytherapy treatment will most definitely enhance its therapeutic effect.

Boronated or gadolinium-containing compounds can be formulated and introduced into the subject systemically according to techniques well known in the art. See, for example, Joel, et al, J Neuro-Oncol 41:213–221, 1999; Coderre, et al, J Neuro-Oncol 33:141–152, 1997; and Chadha, et al, Int J Radiat Oncol Biol Phys 40:829–834, 1998. Suitable neutron capture therapy compounds include p-boronophenylalanine, sodium borocaptate, gadopentic acid, neutral macrocyclic Gd complex (Gadobutrol™), gadodiamide hydrate, gadopentetate dimeglumine, and the like.

In an alternative embodiment, the boronated or gadolinium containing compounds can be directly delivered to the tumor cells via the same burr holes as used for inserting the $^{252}$Cf source. This intra-tumoral drug delivery method has the advantage of having less stringent pharmacokinetic requirements, and therefore results in high concentration in tumor cells compared to systemic drug devlivery method that is used in a NCT treatment The invention will now be described in greater detail by reference to the following non-limiting examples.

EXAMPLES

Patients with Grade III or Grade IV (glioblastoma multiforme) astrocytomas may be treated. Patients referred for brachytherapy may have first undergone a craniotomy with resection of their tumor. Patients eligible for brachytherapy treatment may be those with tumors in either the frontal, temporal, parietal, or occipital lobe. Patients with primary brain stem tumors may be excluded. There may be two treatment groups:

Group 1—Patients in this group have undergone surgical excision (debulking) of their tumor days or weeks prior to brachytherapy. Patients in this group may include those who have not received formal external beam radiation therapy. Prior to brachytherapy, all patients in this group may undergo an MRI of the brain with and without a gadolinium-based contrast agent. The MRI either shows gadolinium enhancement indicative of tumor re-growth or no gadolinium enhancement. In either instance, the radiation sources may be implanted circumferentially around the tumor resection margins. The number of radiation sources internally placed depends on the volume of tumor resection. Areas of the brain which enhance with gadolinium may be specifically targeted for placement of the radiation source. Only patients with a Karnovsky rating greater than 70 are treated. The mechanism by which the source will be implanted is described below.

Group 2—Patients in this group may include those who have documented evidence of tumor re-growth despite one or more craniotomies, radiation therapy, or chemotherapy. Patients in this group must demonstrate areas of tumor recurrence as evidenced by gadolinium enhancement on their MRI. If there is concern as to whether the enhancement seen on an MRI reflects tumor re-growth or radiation necrosis, a biopsy of the enhancing area may be performed prior to treatment in order to insure that tumor is in fact present. Areas of enhancement verified to represent tumor re-growth may be targeted for internal placement of the radiation source as described below. Only patients with a Karnovsky rating greater than 70 are treated.

Craniotomy Procedure—As referred to above, patients undergoing source placement will have, in all instances, undergone a craniotomy for debulking of their tumor. Patients undergoing a craniotomy are anesthetized with general anesthesia. In most instances they undergo placement of a central venous line to measure cardiovascular status during the operative procedure. The day prior to surgery, the patient undergoes a CT scan, and the radiologist performing the exam marks the scalp outlining the margins of the tumor to guide the neurosurgeon in terms of placement of the scalp flap to be used. On the day of surgery, the scalp of the affected region of the brain is shaved and then prepped and draped in a sterile fashion. The scalp is incised with a No. 10 blade. Raney clips are applied to the scalp margins for hemostasis.

A free bone flap is accomplished through the use of burr holes made by a craniotome or a power drill (either the Midas-Rex or another power-assisted drill). The dura is coagulated with bipolar electrocautery and then incised with a No. 11 blade. The dural flap is reflected toward the appropriate sinus and the cortical surface of the brain inspected. The cortical surface of the brain is coagulated with bipolar electroautery and then incised with a No. 11 blade. Dissection is carried out through the white matter and the brain tumor will be identified. A biopsy forceps is used to collect portions of the tumor for a frozen section diagnosis to confirm malignancy. The surgeon will proceed to perform a gross total removal of the tumor when it is deemed that removal can be done safely. A Cavitron, made by S B Medical, may be used for Tumor resection. Bleeding in the tumor margins is controlled with bipolar electrocautery and through the use of gel foam and Avitene made by MedChem Products, Inc. subsidiary of CR Bard, Inc. Upon successful removal of the tumor, the tumor margins of the cavity created are lined with Surgi-cel made by Johnson & Johnson. The dura is closed with interrupted 4-0 Neurolon sutures. The bone flap is re-secured with either plates or 2-0 silk sutures. The muscle and galea are closed with 4-0 Neurolon sutures and the skin closed with a 4-0 nylon stitch.

Neutron Therapy Procedure—Delivery of the neutron emitting source to the site of the tumor is accomplished through the use of catheters (Cook, or Codman Co.) or the catheters described in U.S. Pat. No. 6,352,500 entitled Neutron Brachytherapy Device and Method that was filed on Sep. 13, 1999. One or more catheters are placed in the tumor site. Localization is done through the use of either conventional stereotactic equipment or using the Stealthstation (Sofamor Danek, Memphis, Tenn.). The Stealthstation is preferred as it does not require the used of a stereotactic frame attached to the patient's skull. The Stealthstation will be used to predetermine the optimal sites of entry on the patient's skull, i.e. those providing the shortest, safest route through the brain tissue to the tumor site. Burr holes are drilled at these sites with a craniotome and one or more catheters through which the neutron emitting source will pass are directed to a point such that the tip of the catheter lies at the site of the tumor.

Once the catheter is in place and the position of the tip verified, the neutron emitting source is delivered by a remote afterloader stored in a room adjacent to the operating room. The neutron emitting source passes from the remote afterloader into the catheter. The radiation source passes directly from the remote afterloader into the catheter and remains in place for a time sufficient to irradiate the tumor cells. The neutron emitting source is then retracted, and the patient treated as described above.

While the invention has been described in detail with reference to certain preferred embodiments thereof, it will be understood that modifications and variations are within the spirit and scope of that which is described and claimed.

What is claimed is:

1. A method of treating a subject having a disorder characterized by the presence of a tumor comprising inserting one or more miniaturized concentrated neutron emitting source(s) into said tumor and maintaining the source(s) in the tumor for a time sufficient to eradicate the cells of the tumor, wherein each of the neutron emitting source(s) has an outer diameter that is about 2 mm or less and about 100 µg or more of californium-252.

2. The method of claim 1, wherein said tumor is malignant.

3. The method of claim 2, wherein said tumor is located in said subject's brain, cervix, oral cavity, esophagus, skin, lung, bladder, pancreas, prostate, intestine, stomach, thyroid gland, ovary, breast, or kidney.

4. The method of claim 2, wherein said tumor is located in said subject's brain.

5. The method of claim 4, wherein said tumor is a glioblastoma, an astrocytoma, a schwannoma, a malignant meningioma, an oligodendroglioma, a medulloblastoma, or a ependymoma.

6. A method of treating a subject having a disorder characterized by the presence of one or more tumors comprising:

surgically removing the majority of said tumor(s); and inserting a miniaturized concentrated neutron emitting source into the space previously occupied by the tumor(s) for a time sufficient to eradicate any tumor cells not surgically removed), wherein the neutron emitting source has a diameter that is 2 mm or less and about 100 µg or more of californium-252.

7. The method of claim 6, wherein said tumor is malignant.

8. The method of claim 7, wherein said tumor is located in said subject's brain, cervix, oral cavity, esophagus, skin, lung, bladder, pancreas, prostate, intestine, stomach, thyroid gland, ovary, breast, or kidney.

9. The method of claim 6, wherein said tumor is located in said subject's brain.

10. The method of claim 9, wherein said tumor is a glioblastoma, an astrocytoma, a schwannoma, a malignant meningioma, an oligodendroglioma, a medulloblastoma, or a ependymoma.

11. The method of claim 1 or claim 6, further comprising localizing a neutron capture compound to the cells of said tumor prior to insertion of said miniaturized neutron source.

12. The method of claim 11, wherein said neutron capture compound comprises boron-10.

13. The method of claim 11, wherein said neutron capture compound comprises gadolinium-157.

14. The method of claim 11, wherein said neutron capture compound is localized to said tumor cells by systemic administration of said compound.

15. The method of claim 11, wherein said neutron capture compound is localized to said tumor cells by direct administration of said compound to said tumor cells.

16. The method of claims 1 or 6, wherein said miniaturized concentrated neutron emitting source is 3–6 mm in length, has an outside diameter of 0.50–2 mm, and contains between 100 µg and 1 mg of californium-252.

17. The method of claim 1 further comprising adjusting a number of neutron emitting source(s) that are inserted according to a desired dose distribution in the tumor.

18. The method of claim 6 further comprising adjusting a number of neutron emitting source that are inserted according to a desired dose distribution in the tumor.

* * * * *